United States Patent
Gliner et al.

(10) Patent No.: US 10,404,093 B2
(45) Date of Patent: Sep. 3, 2019

(54) USING LOCATION TRANSMISSION SIGNALS FOR CHARGING A WIRELESS MEDICAL TOOL OF AN ELECTROMAGNETIC NAVIGATION SYSTEM

(71) Applicant: BIOSENSE WEBSTER (ISRAEL) LTD., Yokneam (IL)

(72) Inventors: Vadim Gliner, Haifa (IL); Yaron Ephrath, Karkur (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 15/498,038

(22) Filed: Apr. 26, 2017

(65) Prior Publication Data

US 2018/0316209 A1    Nov. 1, 2018

(51) Int. Cl.
| | | |
|---|---|---|
| *A61B 5/06* | (2006.01) | |
| *H02J 7/00* | (2006.01) | |
| *H02J 7/02* | (2016.01) | |
| *A61B 17/00* | (2006.01) | |
| *A61B 34/20* | (2016.01) | |
| *H01F 38/14* | (2006.01) | |

(Continued)

(52) U.S. Cl.
CPC .............. *H02J 7/025* (2013.01); *A61B 5/062* (2013.01); *A61B 34/20* (2016.02); *H01F 38/14* (2013.01); *H02J 7/0042* (2013.01); *H02J 50/10* (2016.02); *H02J 50/40* (2016.02); *A61B 2017/00734* (2013.01); *A61B 2034/2051* (2016.02); *A61B 2560/0219* (2013.01)

(58) Field of Classification Search
CPC ............... H02J 7/025; H02J 7/50; H02J 17/00
See application file for complete search history.

(56) References Cited

U.S. PATENT DOCUMENTS

| | | |
|---|---|---|
| 5,391,199 A | 2/1995 | Ben-Haim |
| 5,443,489 A | 8/1995 | Ben-Haim |
| 5,558,091 A | 9/1996 | Acker et al. |

(Continued)

FOREIGN PATENT DOCUMENTS

WO    2007070944 A1    6/2007

OTHER PUBLICATIONS

Extended European Search Report dated Aug. 1, 2018 for the European Patent Application No. 18169288.0.

*Primary Examiner* — David V Henze-Gongola
(74) *Attorney, Agent, or Firm* — Volpe and Koenig, P.C.

(57) ABSTRACT

An electromagnetic navigation system having a wireless, battery-powered medical tool is provided. The system charges the medical tool using energy from the same magnetic fields used to locate the tool in 3-D space. The system includes one or more wireless transmission devices which generate the magnetic fields. The medical tool includes a receiving coil which generates electrical signals indicative of a location of the tool in response to receiving the magnetic fields. The tool also includes a wireless interface which provides electrical signals for processing to determine the location of the tool in 3-D space and a battery which supplies power to the tool. The tool also includes one or more charging coils, electrically connected to the battery. Each charging coil receives energy from the magnetic fields passing through a charging coil surface and supplies the energy to the battery to charge the battery.

20 Claims, 9 Drawing Sheets

(51) Int. Cl.
*H02J 50/10* (2016.01)
*H02J 50/40* (2016.01)

(56) References Cited

U.S. PATENT DOCUMENTS

| | | | |
|---|---|---|---|
| 6,172,499 | B1 | 1/2001 | Ashe |
| 6,177,792 | B1 | 1/2001 | Govari et al. |
| 6,266,551 | B1 | 7/2001 | Osadchy et al. |
| 6,690,963 | B2 | 2/2004 | Ben-Haim et al. |
| 6,788,967 | B2 | 9/2004 | Ben-Haim et al. |
| 9,136,729 | B2 * | 9/2015 | Ashinghurst ......... H02J 7/0042 |
| 2003/0078003 | A1 * | 4/2003 | Hunter .................... A61B 5/06 |
| | | | 455/41.1 |
| 2003/0085684 | A1 * | 5/2003 | Tsukamoto .......... A61N 1/3787 |
| | | | 320/108 |
| 2005/0099290 | A1 | 5/2005 | Govari |
| 2007/0032697 | A1 | 2/2007 | Shimizu et al. |
| 2007/0290654 | A1 * | 12/2007 | Govari .................... H02J 50/12 |
| | | | 320/155 |
| 2008/0183188 | A1 | 7/2008 | Carls et al. |
| 2008/0300459 | A1 * | 12/2008 | Kimura .............. A61B 1/00016 |
| | | | 600/118 |
| 2014/0197784 | A1 * | 7/2014 | Boldt ..................... H02J 7/025 |
| | | | 320/108 |
| 2015/0119686 | A1 | 4/2015 | Govari et al. |
| 2015/0305823 | A1 * | 10/2015 | Claus .................... A61B 34/20 |
| | | | 600/424 |
| 2016/0192989 | A1 | 7/2016 | Aman |

\* cited by examiner

USING LOCATION TRANSMISSION SIGNALS FOR CHARGING A WIRELESS MEDICAL TOOL OF AN ELECTROMAGNETIC NAVIGATION SYSTEM

SUMMARY

An electromagnetic navigation system is provided that includes a first wireless transmission device having one or more emitter coils. Each of the one or more emitter coils is driven by a different frequency and each is configured to generate a magnetic field. The system includes a wireless, battery-powered tool configured to perform a medical procedure on a patient. The tool includes a receiving coil, disposed at the tool, configured to receive one or more magnetic fields emitted by the one or more emitter coils and generate electrical signals indicative of a location of the tool in response to receiving the one or more magnetic fields. The tool also includes a wireless interface configured to provide the electrical signals for processing to determine the location of the tool in three-dimensional (3-D) space. The tool also includes a battery configured to supply power to the tool and one or more charging coils electrically connected to the battery, each of the one or more charging coils configured to (i) receive energy from the one or more magnetic fields passing through a surface of the one or more charging coils and (ii) supply the energy to the battery to charge the battery.

A wireless, battery-powered medical tool for use with an electromagnetic navigation system is provided. The medical tool includes a receiving coil, disposed at the medical tool, configured to receive one or more magnetic fields emitted by the one or more emitter coils and generate electrical signals indicative of a location of the medical tool in response to receiving the one or more magnetic fields. The medical tool also includes wireless interface configured to wirelessly provide the electrical signals for processing to determine the location of the medical tool in 3-D space. The tool also includes a battery configured to supply power to the medical tool and one or more charging coils electrically connected to the battery. Each of the one or more charging coils is disposed at the medical tool and configured to (i) receive energy from the one or more magnetic fields passing through a surface of the one or more charging coils and (ii) supply the energy to the battery to charge the battery.

A method of charging a wireless, battery-powered medical tool is provided. The method includes receiving one or more magnetic fields at a receiving coil disposed at the medical tool and receiving the one or more magnetic fields at one or more charging coils electrically connected to a battery disposed at the medical tool. The method also includes generating, by the receiving coil, electrical signals indicative of a location of the medical tool in 3-D space in response to receiving the one or more magnetic fields. The method also includes providing, via a wireless interface disposed at the medical tool, the electrical signals for processing to determine the location of the medical tool in 3-D space. The method further includes supplying, by the one or more charging coils, power to the battery via energy received from the one or more magnetic fields passing through a surface of the one or more charging coils.

BRIEF DESCRIPTION OF THE DRAWINGS

A more detailed understanding can be had from the following description, given by way of example in conjunction with the accompanying drawings wherein.

DETAILED DESCRIPTION

Electromagnetic navigation systems are used to determine a location of a medical tool in 3-D space within patient anatomy. Based on the determined location, anatomical information of the patient is displayed to medical personnel. In some electromagnetic navigation systems, the medical tools are wireless connected to the system components. In these wireless systems, medical personnel, such as ear, nose and throat (ENT) physicians and cardiologists, use battery-powered tools, such as catheters, for performing medical procedures on patient anatomy.

The procedures typically involve hours of delicate maneuvering by the physician. To prevent a tool from a power failure during a procedure, sufficient power is continuously supplied from the battery to the tool for the duration of the procedure. Accordingly, the size and weight of the battery mounted to the tool to provide the continuous power (e.g., capacitance) is often cumbersome for the physician, negatively impacting the ability of the physician to maneuver the tool.

The present application discloses systems, apparatuses and methods of charging tools by utilizing energy from magnetic fields that are generated by the same wireless transmission devices that generate the magnetic fields used to locate the tool in 3-D space. The tool includes one or more charging coils which receive energy to charge the battery when the magnetic field, generated by the wireless signals, passes through the charging coils (e.g., the surfaces of the charging coils). The charging coils are wound or looped around one or portions of the tool to provide increased surface area for receive energy for charging the tool. The charging coils provide ample power for the tool complete the lengthy procedures without increasing battery size, facilitating light and ergonomic tools for smooth maneuverability.

Embodiments include providing wireless transmission signals from one or more magnetic field generating devices. For example, a magnetic field generating device includes a location pad, having one or more emitting coils, which is provided adjacent (e.g., below) patient anatomy to facilitate locating the tool in 3-D space. In one embodiment, the location pad includes a plurality of emitting coils disposed at different locations of a horseshoe shaped field generating device. In addition or alternative to the location pad, one or more other wireless transmission devices can also be provided to transmit wireless signals.

Figure 1:
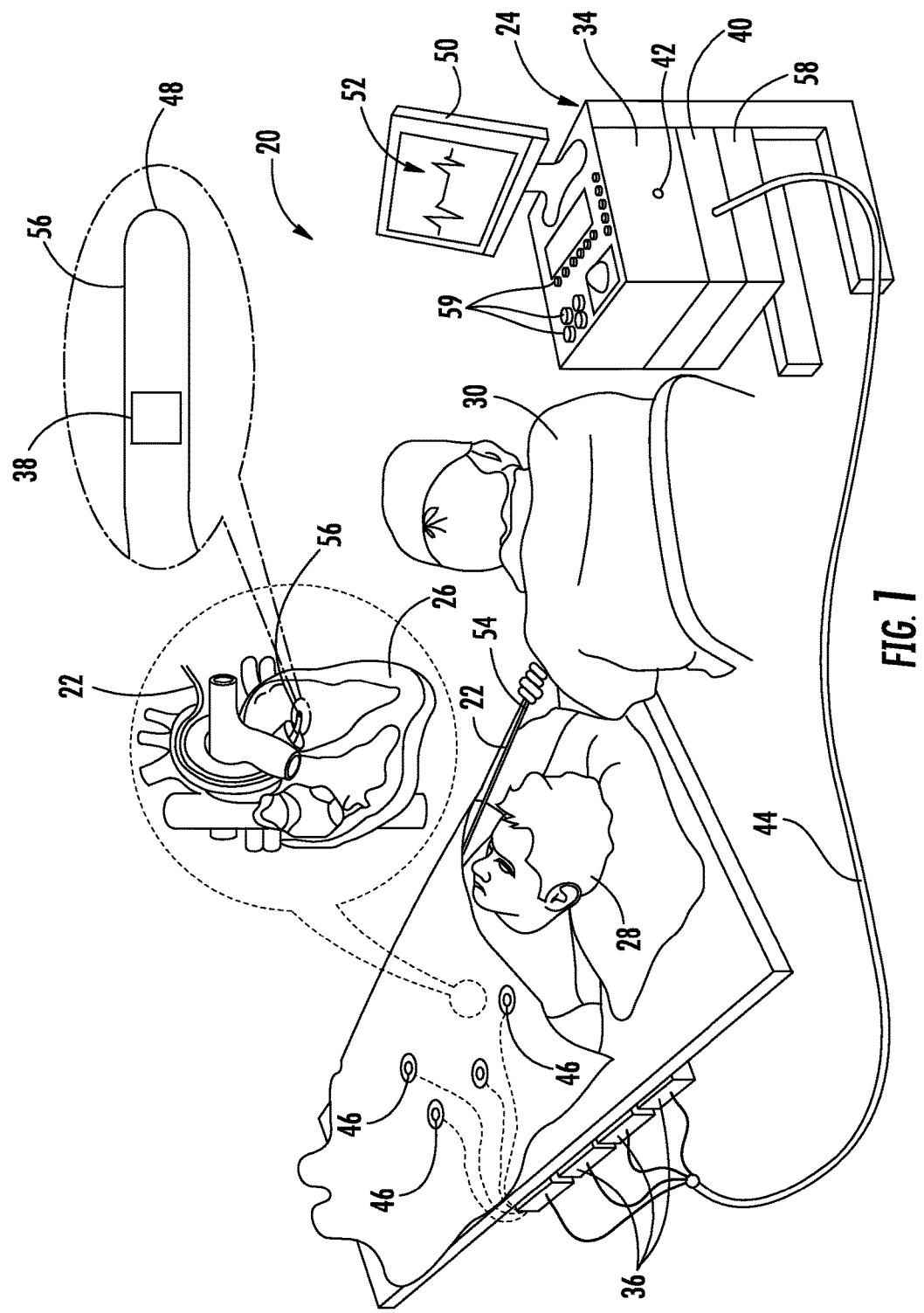
FIG. 1 is an illustration of an example medical system for navigating a tool in 3-D space according to embodiments disclosed herein.

Referring now to FIG. 1, an illustration of an example medical system 20 is shown that may be used to generate and display information 52 (e.g., a chart, anatomical models of a portion of a patient and signal information). Tools (i.e., medical tools), such as tool 22, can be any tool used for diagnostic or therapeutic treatment, such as for mapping electrical potentials in a heart 26 of a patient 28. Alternatively, tools may be used, mutatis mutandis, for other therapeutic and/or diagnostic purposes of different portions of anatomy, such as in the heart, lungs or other body organs, such as the ear, nose, and throat (ENT). Tools may include, for example, probes, catheters, cutting tools and suction devices.

An operator 30 may insert the tool 22 into a portion of patient anatomy, such as the vascular system of the patient 28 so that a tip 56 of the tool 22 enters a chamber of the heart 26. The control console 24 may use magnetic position sensing to determine position coordinates of the tool (e.g., coordinates of the tip 56) in 3-D space inside the heart 26. To determine the position coordinates, a driver circuit 34 in the control console 24 may drive, via connector, 44, field generators 36 to generate magnetic fields within the anatomy of the patient 28.

The field generators 36 include one or more emitter coils (not shown in FIG. 1), placed at known positions external to the patient 28, which are configured to generate magnetic fields in a predefined working volume that contains a portion of interest of the patient anatomy. Each of the emitting coils is driven by a different frequency to emit a constant magnetic field in 3-D space. For example, in the example medical system 20 shown in FIG. 1, one or more emitter coils can be placed below the torso of the patient 28 and each configured to generate magnetic fields in a predefined working volume that contains the heart 26 of the patient.

As shown in FIG. 1, a magnetic field location sensor 38 is disposed at the tip 56 of tool 22. The magnetic field location sensor 38 is used to determine the position of the receiving coil in 3-D space and generate electrical signals based on the amplitude and phase of the magnetic fields. Although the magnetic field location sensor 38 is disposed at the tip 56 of tool 22, a tool can include one or more magnetic field location sensors each disposed at any portion of the tool.

The signals are wirelessly communicated to the control console 24 via a wireless communication interface (e.g., interface 312 shown at FIG. 3) at the tool 22 that may communicate with a corresponding input/output (I/O) interface 42 in the control console 24. The wireless communication interface 312 and the I/O interface 42 may operate in accordance with any suitable wireless communication standard that is known in the art, such as for example, infrared (IR), radio frequency (RF), Bluetooth, one of the IEEE 802.11 family of standards (e.g., Wi-Fi), or the HiperLAN standard. The body surface electrodes 46 may include one or more wireless sensor nodes integrated on a flexible substrate. The one or more wireless sensor nodes may include a wireless transmit/receive unit (WTRU) enabling local digital signal processing, a radio link, and a miniaturized rechargeable battery, as described in more detail below.

The I/O interface 42 may enable the control console 24 to interact with the tool 22, the body surface electrodes 46 and the position sensors (not shown). Based on the electrical impulses received from the body surface electrodes 46 and the electrical signals received from the tool 22 via the I/O interface 42 and other components of medical system 20, the signal processor 40 may determine the location of the tool in 3-D space and generate the display information 52, which may be shown on a display 50.

The signal processor 40 is configured to process the signals to determine the position coordinates of the tip 56 in 3-D space, including both location and orientation coordinates. The method of position sensing described hereinabove is implemented in the CARTO mapping system produced by Biosense Webster Inc., of Diamond Bar, Calif., and is described in detail in the patents and the patent applications cited herein.

The magnetic field location sensor 38 transmits a signal to the control console 24 which indicates location coordinates of the tool 22 (e.g., location coordinates of the tip 56) in 3-D space. The magnetic field location sensor 38 may include one or more miniature receiving coils (e.g., receiving coil(s) 304 shown in FIG. 3) and may include multiple miniature coils oriented along different axes. Alternatively, the magnetic field location sensor 38 may include another type of magnetic sensor or position transducers of other types, such as impedance-based or ultrasonic location sensors. Although FIG. 1 shows the tool 22 having a single location sensor, embodiments may include tools with more than one location sensor.

Magnetic position tracking techniques are described, for example, in U.S. Pat. Nos. 5,391,199, 5,443,489, 6,788,967, 6,690,963, 5,558,091, 6,172,499 6,177,792, whose disclosures are incorporated herein by reference.

The tool 22 may also include an electrode 48 coupled to the tip 56 and configured to function as an impedance-based position transducer. Additionally or alternatively, the electrode 48 may be configured to measure a certain physiological property, for example the local surface electrical potential (e.g., of cardiac tissue) at one or more locations. The electrode 48 may be configured to apply RF energy to ablate endocardial tissue in the heart 26.

The signal processor 40 may be included in a general-purpose computer, with a suitable front end and interface circuits for receiving signals from the tool 22 and controlling the other components of the control console 24. The signal processor 40 may be programmed, using software, to perform the functions that are described herein. The software may be downloaded to the control console 24 in electronic form, over a network, for example, or it may be provided on non-transitory tangible media, such as optical, magnetic or electronic memory media. Alternatively, some or all of the functions of the signal processor 40 may be performed by dedicated or programmable digital hardware components.

In the example shown at FIG. 1, the control console 24 is connected, via cable 44, to body surface electrodes 46, each of which are attached to patient 28 using patches (e.g., indicated in FIG. 1 as circles around the electrodes 46) that adhere to the skin of the patient. In addition or alternative to the patches, body surface electrodes 46 may also be positioned on the patient using articles worn by patient 28 which include the body surface electrodes 46 and may also include one or more position sensors (not shown) indicating the location of the worn article. For example, body surface electrodes 46 can be embedded in a vest that is configured to be worn by the patient 28. During operation, the body surface electrodes 46 assist in providing a location of the tool (e.g., catheter) in 3-D space by detecting electrical impulses generated by the polarization and depolarization of cardiac tissue and transmitting information to the control console 24, via the cable 44. The body surface electrodes 46 can be equipped with magnetic location tracking and can help identify and track the respiration cycle of the patient 28.

Additionally or alternatively, the tool 22, the body surface electrodes 46 and other sensors (not shown) may communicate with the control console 24 and one another via a wireless interface. For example, U.S. Pat. No. 6,266,551, whose disclosure is incorporated herein by reference, describes, inter alia, a wireless catheter, which is not physically connected to signal processing and/or computing apparatus and is incorporated herein by reference. Rather, a transmitter/receiver is attached to the proximal end of the catheter. The transmitter/receiver communicates with a signal processing and/or computer apparatus using wireless communication methods, such as IR, RF, Bluetooth, or acoustic transmissions.

During the diagnostic treatment, the signal processor 40 may present the display information 52 and may store data representing the information 52 in a memory 58. The memory 58 may include any suitable volatile and/or non-volatile memory, such as random access memory or a hard disk drive. The operator 30 may be able to manipulate the display information 52 using one or more input devices 59. Alternatively, the medical system 20 may include a second operator that manipulates the control console 24 while the operator 30 manipulates the tool 22. It should be noted that the configuration shown in FIG. 1 is exemplary. Any suitable configuration of the medical system 20 may be used and implemented.

Figure 2:
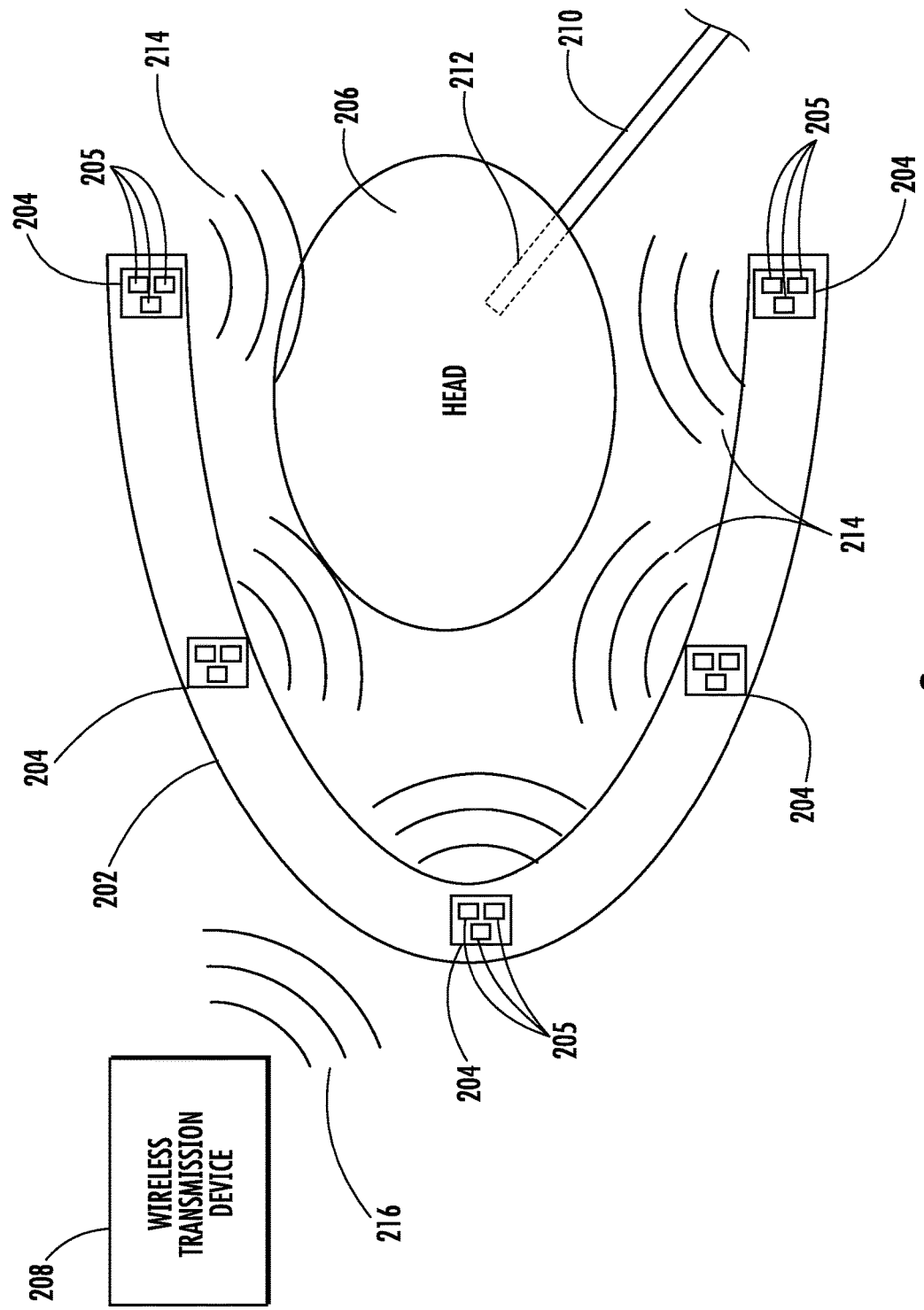
FIG. 2 is an illustration of components of an example electromagnetic navigation system for use with embodiments described herein.

FIG. 2 is an illustration of example components of a portion of an electro-navigation navigation system for use with embodiments described herein. As shown in FIG. 2, a wireless transmission device 202 is positioned adjacent to a head 206 of a patient. As shown in FIG. 2, the wireless transmission device 202 is a horseshoe shaped device (i.e., location pad) which includes a plurality of wireless transmitters 204 each having three emitter coils 205. Each of the emitter coils 205 is driven by a different frequency. That is, each of the emitter coils 205 is configured to radiate at a different frequency and emit a wireless signal (e.g., Wi-Fi signals) at its corresponding frequency.

The shape of the wireless transmission device 202 is merely exemplary. Electromagnetic magnetic navigation systems may include field generating devices shaped differently from the device 202 shown in FIG. 2. The number of wireless transmitters 204 and the locations of the wireless transmitters 204 shown in FIG. 2 are exemplary. Wireless transmission devices may include any number of wireless transmitters each having any number of emitter coils, including a single emitter coil. Wireless transmitters 204 may include locations different from the locations of the wireless transmitters 204 shown in FIG. 2. Alternative, or in addition, to the wireless transmission device (i.e., the location pad) 202, magnetic navigation systems can include one or more other wireless transmission devices (e.g., a Wi-Fi emitter, such as an access point) configured to provide wireless transmission signals, such as wireless transmission device 208.

As shown in FIG. 2, a tool 210 is placed inside a patient (i.e., head 206). As shown, the wireless transmission signals 214 from wireless transmitters 204 and wireless transmission signals 216 from wireless transmission device 208 propagate toward the location of the tip 212 of tool 210. Based on the amplitude and phase of the magnetic fields generated by the wireless transmission signals 214 and 216, a receiving coil (e.g., receiving coil(s) 310 shown in FIG. 3) in the tool 210 (e.g., in the tip 212) is configured to generate electrical signals (not shown) to be processed by signal processer (e.g., signal processor 40 shown in FIG. 1) for determining the location of the receiving coil 310 in 3-D space.

The location of wireless transmission device 208 and tool 210 shown in FIG. 2 is merely exemplary. Magnetic navigation systems can include wireless transmission devices, configured to provide magnetic fields to a portion of interest of the patient anatomy, at locations different from the location of wireless transmission device 208 and tool 210 shown in FIG. 2.

Figure 3:
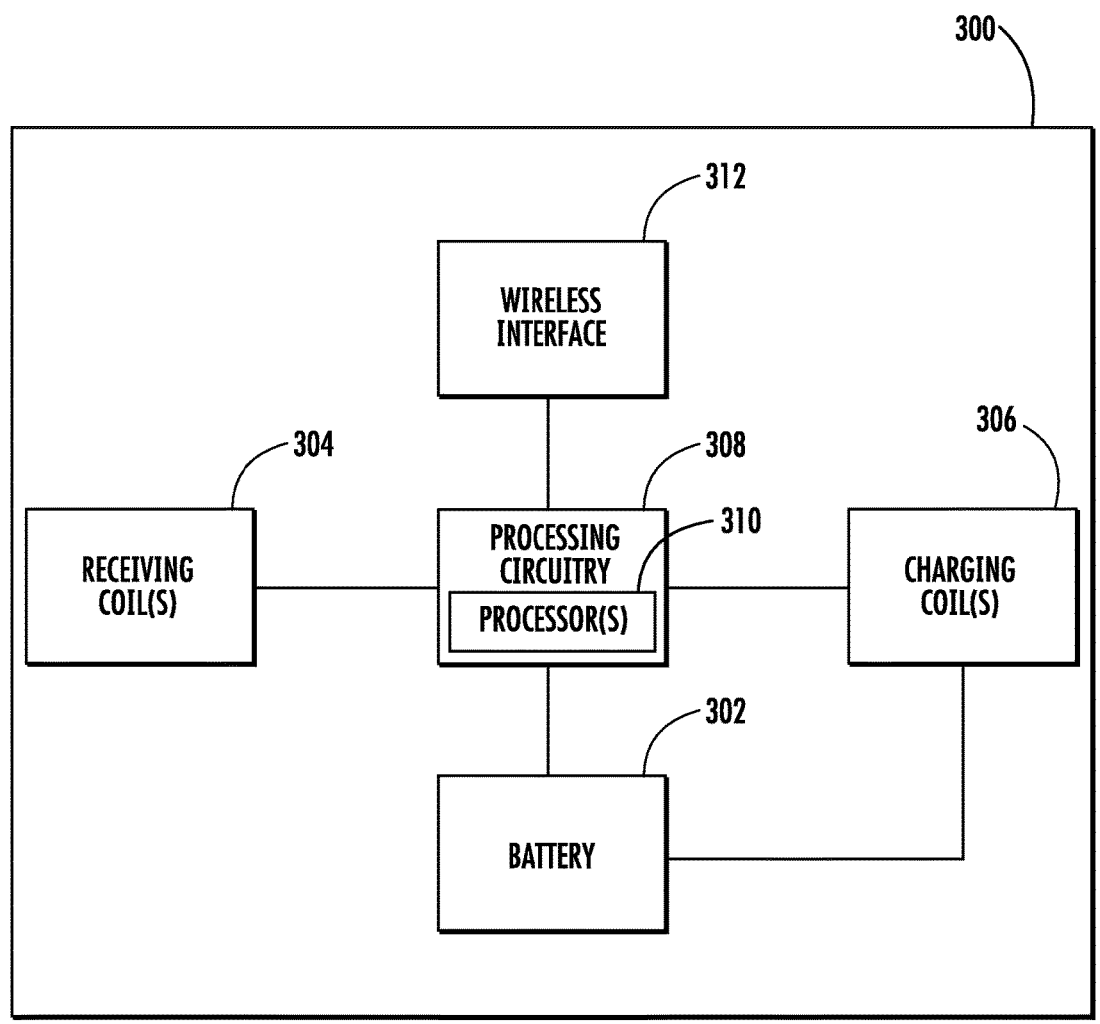
FIG. 3 is a block diagram illustrating components of an example wireless, battery-powered medical tool for use with electromagnetic navigation systems described herein.

FIG. 3 is a block diagram illustrating components of an example wireless, battery-powered medical tool 300 for use with electromagnetic navigation systems described herein. As shown in FIG. 3, the medical tool 300 includes a battery 302, one or more receiving coils 304 and one or more charging coils 306. The tool 300 also includes processing circuitry 308 having one or more processors 310. The tool 300 also includes wireless communication interface 312.

The battery 302 is configured to supply power to one or more components of the tool 300, such as processing circuitry 308 and wireless communication interface 312 shown in FIG. 3 as well as other components (e.g., motors, actuators) not shown. The battery 302 may be removable or fixed to the tool 300.

The one or more receiving coils 304 are configured to receive one or more magnetic fields generated by wireless transmission signals (e.g., magnetic fields emitted by one or more emitter coils 205 of wireless transmitters 204 and/or wireless transmission device 208 shown in FIG. 2) passing through the one or more receiving coils 304 (e.g., through a surface of the one or more receiving coils 304). In response to receiving the magnetic fields, electrical currents electrical signals are generated (i.e., current is induced) in the one or more receiving coils 304. The amplitudes of the electrical signals (or alternatively, time-varying voltages across the one or more receiving coils 304) are dependent on the location and orientation of the one or more receiving coils 304 relative to the location and orientation of one or more emitter coils (e.g., one or more emitter coils 205 of wireless transmitters 204).

Processing circuitry 310 may include one or more processors 310 configured to process the electrical signals generated by the one or more receiving coils 304. Wireless communication interface 312 (e.g., wireless network interface controller (NIC)) is configured to wirelessly transmit the processed electrical signals (e.g., to the control console 24) to determine the location of the tool 300 in 3-D space. The wireless communication interface 312 may communicate with a corresponding input/output (I/O) interface 42 in the control console 24.

As shown in FIG. 3, the tool also includes one or more charging coils 306. The one or more charging coils 306 are electrically connected to the battery 302 to charge the battery. For example, the one or more charging coils 306 may be electrically connected to a power terminal of the battery 302. The one or more charging coils 306 may be electrically connected to the battery 302 via other circuitry (e.g., a rectifier) not shown.

As described above, the one or more magnetic fields passing through one or more receiving coils 304 are used to determine the location of the tool 300 in 3-D space. In addition to facilitating the determination the location of the tool 300, the magnetic fields also include energy which is utilized, as described in detail below, to supply power to the battery 302. When a number of magnetic field lines (i.e., magnetic flux) of a magnetic field pass through a coil (e.g., through a receiving coil 304 or a charging coil 306), energy is transferred from the magnetic field to the coil. The one or more charging coils 306 are used to charge the battery 302 via energy from magnetic fields generated by the same wireless transmission devices (e.g., emitter coils 205 of wireless transmitters 204 and/or wireless transmission device 208 shown in FIG. 2) that generate the magnetic fields used to locate the tool 300 in 3-D space (e.g., via the one or more receiving coils 304).

The amount of energy a coil receives from the magnetic field is proportionate to the size of the coil (e.g., proportionate to the area of the surface of the coil). The electromagnetic location sensor, such as sensor 38 shown in FIG. 1, is relatively small (i.e., the surface area of the receiving coil is small) as its purpose is to indicate an accurate of the tool in 3-D space. Accordingly, a small portion of the energy of the magnetic field generated by the wireless signals is transferred to the one or more receiving coils 304. The one or more charging coils 306 provide power to the battery 302 by utilizing the energy from the magnetic fields which is not transferred to the one or more receiving coils 304. That is, the one or more charging coils 306 are used to charge the battery 302 via energy from magnetic fields that are generated by the same wireless transmission devices (e.g., wireless transmitters 204 and/or wireless transmission device 208 shown in FIG. 2) which generate the magnetic fields used to locate the tool 300 in 3-D space.

In addition to processing the electrical signals generated by the one or more receiving coils 304, the one or more processors 310 of processing circuitry 310 may also be used to control the power (e.g., amount of power) delivered by the charging coil 304 to the battery 302.

Figure 4:
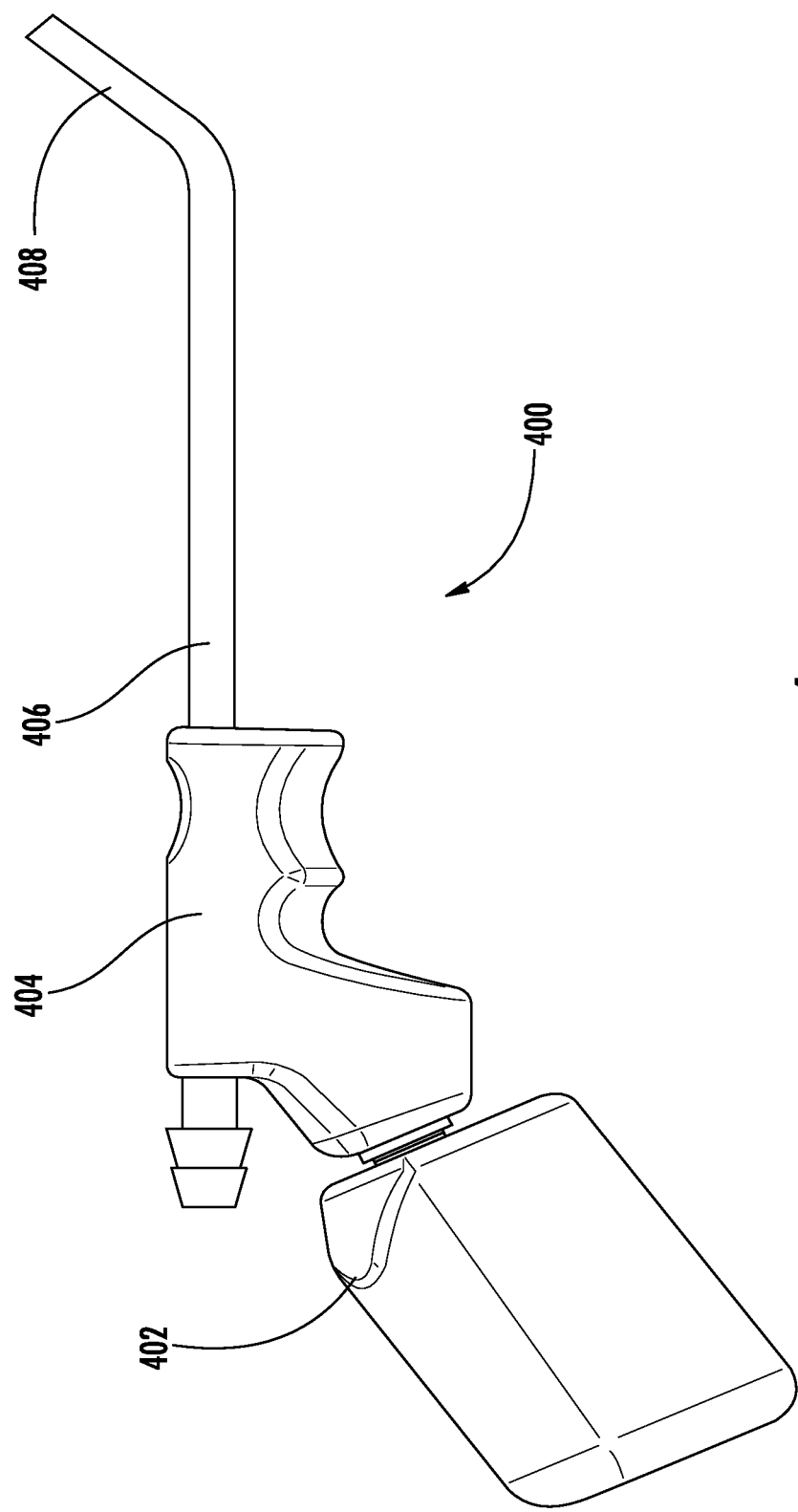
FIG. 4 is an illustration of an example wireless, battery-powered tool for use with wireless electromagnetic navigation systems described herein.

FIG. 4 is an illustration of an example wireless, battery-powered tool 400 for use with wireless electromagnetic navigation systems described herein. As shown in FIG. 4, the wireless tool 400 includes a battery 402, a handle 404 and a probe portion 406 which includes a tip 408. The battery 402 is configured to supply power for driving tool components, such as processing circuitry 308 (e.g., processor(s) 310 and other components not show, such as sampling components, analog to digital converters, motors and actuators) and communication components (e.g., wireless communication interface 312).

The handle 404 is configured to be held by medical personnel for maneuvering the tool in 3-D space. The probe portion 406 is configured to be inserted into a patient during a medical procedure. As shown in the example tool 400 at FIG. 4, the handle 404 is coupled between the battery 402 and the probe portion 406. The shape of the tool 400 and the shape and location of its components shown in FIG. 4 are merely exemplary. Tools may be shaped differently from the tool 400 shown in FIG. 4. Further, tool components may include shapes and locations different from those shown in FIG. 4.

Figure 5:
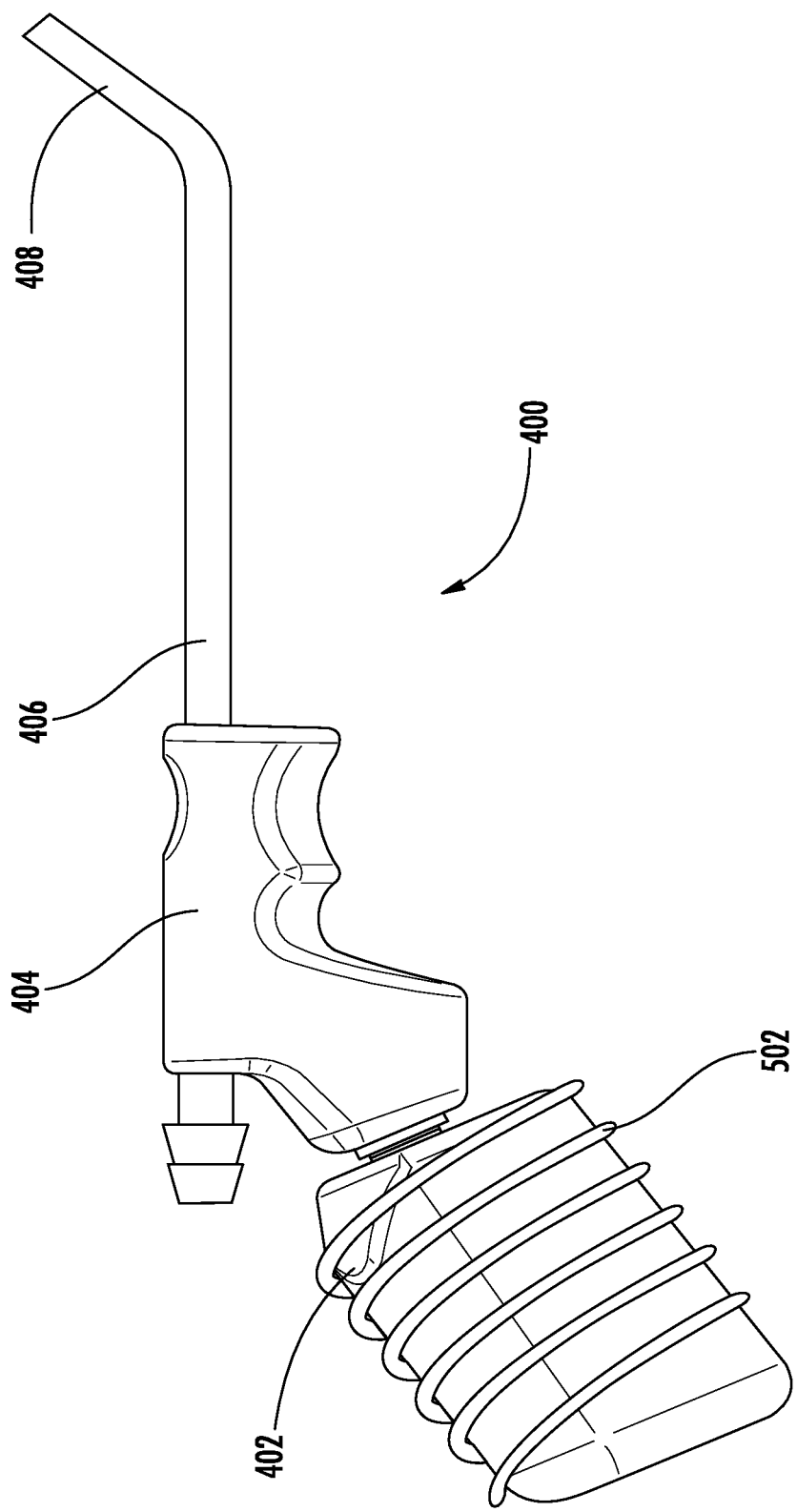
FIG. 5 is an illustration of an example wireless, battery-powered tool shown in FIG. 4 having a single charging coil disposed at the battery.
Figure 6:
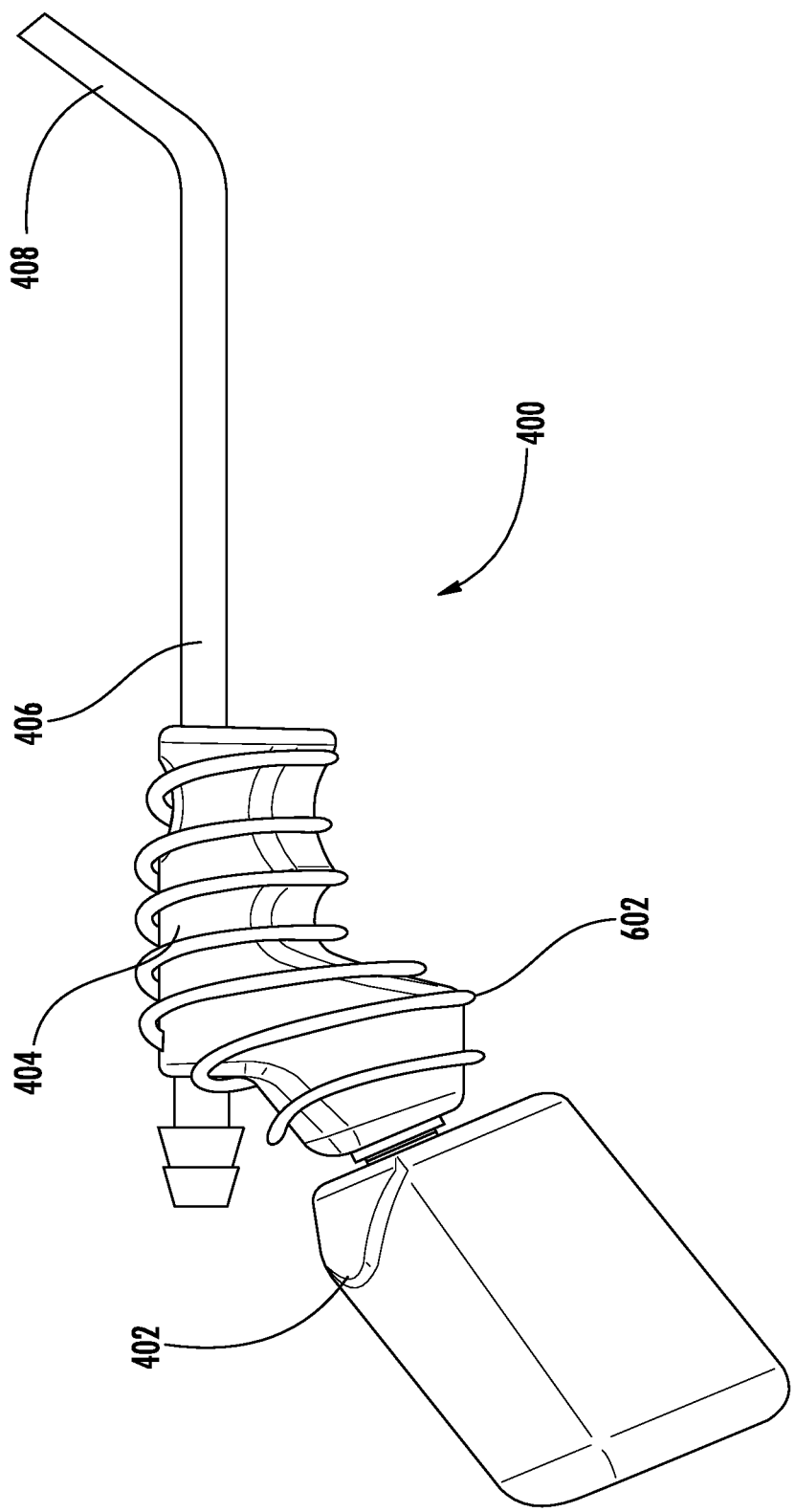
FIG. 6 is an illustration of the example wireless, battery-powered tool shown in FIG. 4 having a single charging coil disposed at the tool handle.
Figure 7:
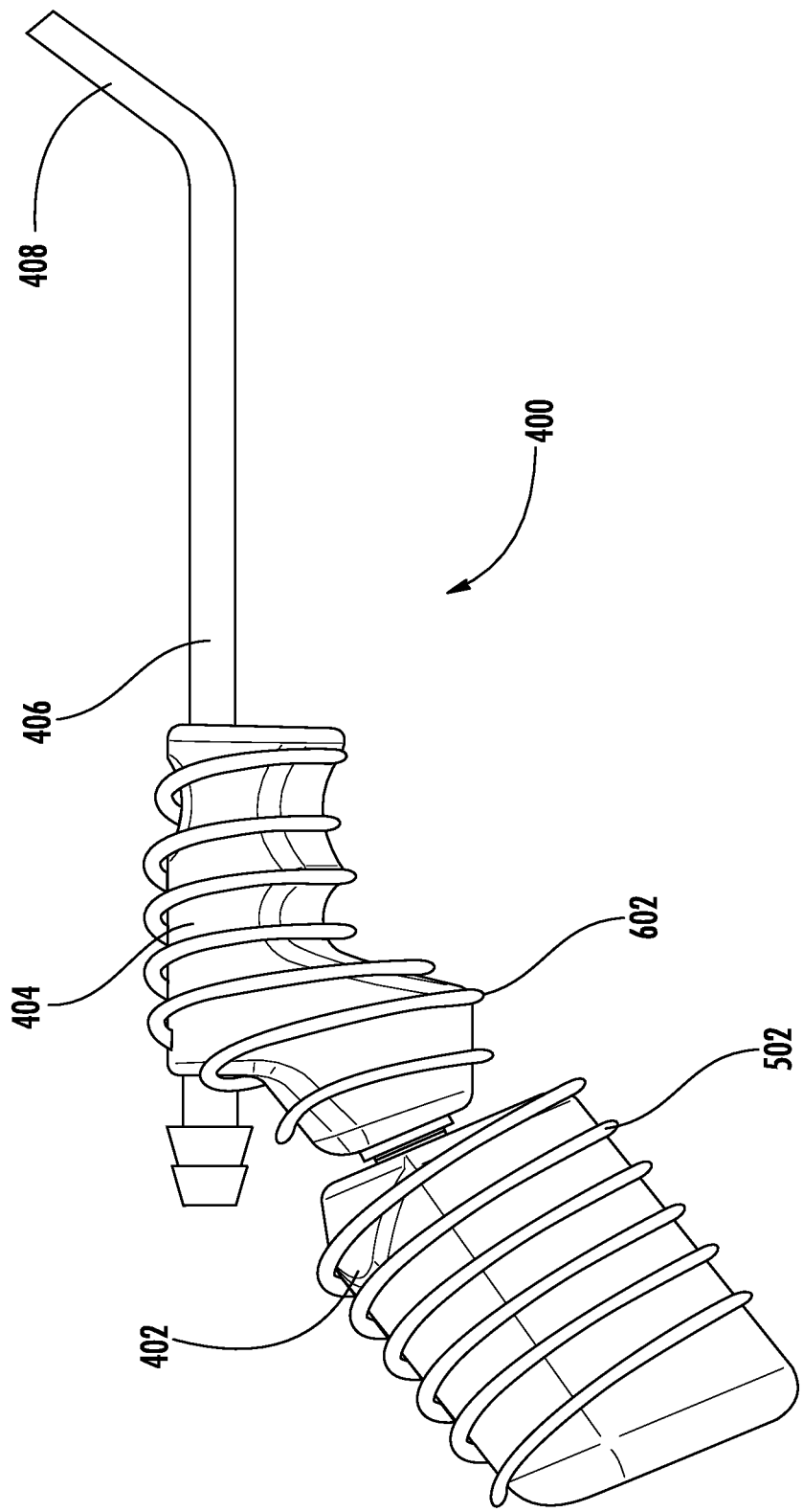
FIG. 7 is an illustration of an example wireless, battery-powered tool shown in FIG. 4 including a pair of charging coils disposed at the battery and the tool handle.

FIGS. 5-7 illustrate different examples of using the wireless, battery-powered tool 400 to charge the battery 402 via energy from magnetic fields which are generated by the same wireless transmission devices which generate the magnetic fields used to locate the tool in 3-D space.

FIG. 5 is an illustration of the example wireless, battery-powered tool 400 shown in FIG. 4 having a single charging coil 502 disposed at the battery 402. The charging coil 502 may be electrically connected to an input terminal (not shown) of the battery 402 for providing electrical power to the battery 402. As shown in FIG. 5, the charging coil 502 is disposed at the battery 402 by being wound (i.e., looped) around the battery 402. Each loop of the charging coil 502 provides additional coil surface area. As described above, an amount of energy a coil receives from a magnetic field is proportionate to the surface area of the coil. Accordingly, the additional coil surface area of the charging coil's loops enables an amount of energy to be transferred from the magnetic field passing through the surface area of the charging coil 502 that is sufficient for providing power to the tool 400 to complete a lengthy procedure (e.g., 2-3 hours). Also, the additional coil surface area facilitates the maneuverability of the tool 400 because the size of the battery, and therefore the size and weight of the tool 400, may be reduced while maintaining or even increasing the available power to be supplied to the tool 400.

FIG. 6 is an illustration of the example wireless, battery-powered tool 400 which includes a single charging coil 602 disposed at the tool handle 404. The charging coil 602 is electrically connected to the battery 402 for providing electrical power to the battery 402. As shown in FIG. 6, the charging coil 602 is wound (i.e., looped) around the tool handle 404. Each loop of the charging coil 602 provides additional coil surface area. Accordingly, a sufficient amount of energy is provided to power the tool 400 while facilitating maneuverability of the tool 400.

FIG. 7 is an illustration of the example wireless, battery-powered tool 400 which includes a pair of charging coils (i.e., the coil 502 shown at FIG. 5 and the coil 602 shown at FIG. 6). Each of the charging coils 502 and 602 is electrically connected to the battery 402 for providing electrical power to the battery 402. As shown, first charging coil 502 is disposed at the battery 402 and second charging coil 602 is disposed at the tool handle 404. The first and second charging coils 502 and 602 are wound (i.e., looped) around a portion of the battery 402 and handle 404, respectively.

The first and second charging coils 502 and 602 provide a sum coil surface area that is larger than the surface area of the charging coils 502 and 602 shown in FIG. 5 and FIG. 6, respectively. Accordingly, the amount of transferrable energy using the pair of charging coils 502 and 602 is greater than the amount of transferrable energy by a single charging coil, such as the single charging coil 502 shown in FIG. 5 and the single charging coil 602 shown in FIG. 6. Therefore, a larger amount of power is available to be supplied to the battery 302.

The number of the charging coils shown in FIGS. 5-7 and their corresponding locations are exemplary. Also, the configuration (e.g., number of loops, length and thickness) of the charging coils 302 and 304 shown in FIGS. 5-7 is also exemplary. Tools may include any number of charging coils. Tools may also include charging coils having different configurations and different locations (e.g., at probe portion 406) from those shown at FIGS. 5-7. The charging coils may include any type of conductive material configured to provide electrical power to the battery 402, such as metals (copper, aluminum, silver), electrolytes, superconductors, semiconductors, plasmas and non-metallic conductors, such as graphite and conductive polymers. The number, size, shape, location and material of the charging coils used for a tool can depend upon different factors, such as tool type, procedure type, estimated time for procedure performed by tool.

In the embodiments shown in FIGS. 5-7, the charging coils 502 and 602 are disposed at the tool 400 by being wound around an outer side of the battery 402 and handle 404. Charging coils may, however, be disposed at a tool by being embedded within a tool component (e.g., a battery or handle) or partially embedded within a tool component.

Figure 8A:
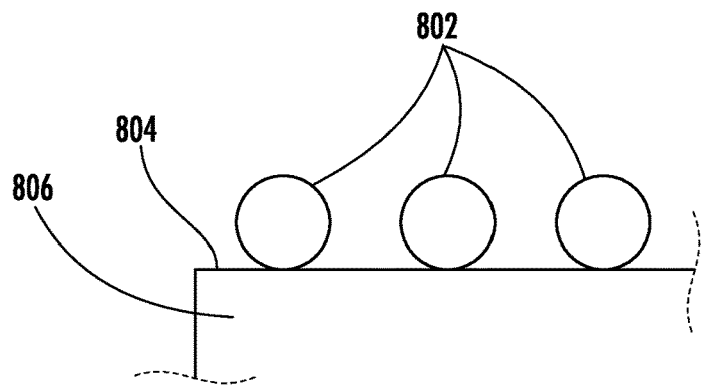
FIG. 8A is a cross sectional view of an exemplary portion of a tool component illustrating charging coil loops wound around an outer side of the tool component.
Figure 8B:
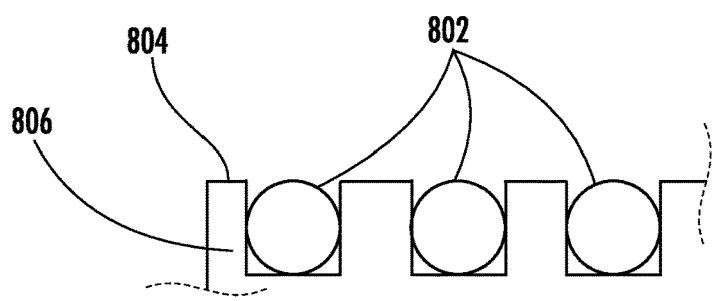
FIG. 8B is a cross sectional view of an exemplary portion of a tool component illustrating charging coil loops embedded in the tool component.
Figure 8C:
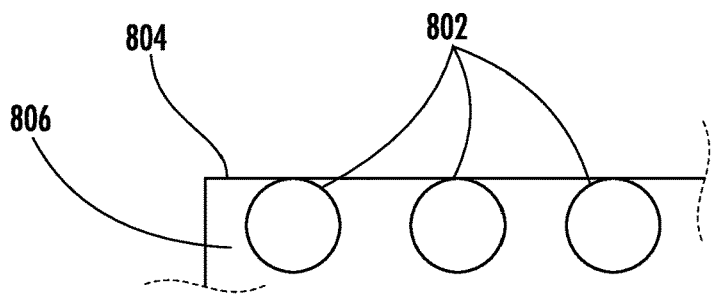
FIG. 8C is a cross sectional view of an exemplary portion of a tool component illustrating charging coil loops located within the tool component.

FIGS. 8A to 8C illustrate different examples of charging coil loops 802 disposed at a tool component 806. For example, FIG. 8A is a cross sectional view of an exemplary portion of tool component 806 illustrating charging coil loops 802 wound around an outer side 804 of the tool component 806. As shown in FIG. 8A, the loops 802 are located on the outer side 804 of a tool component 806. Because the coil loops are exposed outside of the tool component 806, attenuation of the energy received by the charging coils 502 and 602 is limited.

FIG. 8B is a cross sectional view of an exemplary portion of a tool illustrating charging coil loops 802 embedded within the tool component 806, such that the charging coil loops 802 are partially exposed. In the example at FIG. 8B, the energy received by the coil loops 802 may be attenuated to some degree by the tool component 806. The configuration of the coil loops 802 in FIG. 8B, however, facilitates partial direct exposure while limiting user contact with the charging coil loops 802.

FIG. 8C is a cross sectional view of an exemplary portion of tool component 806 illustrating charging coil loops 802 located within the tool component 806. The configuration of the coil loops 802 shown in FIG. 8C may extend the life of the coil (e.g., by preventing user contact). Embodiments may include one charging coil disposed at one tool component according to one of the examples shown in FIG. 8A to 8C and another charging coil disposed at another tool component according to another one of the examples shown in FIG. 8A to 8C. Embodiments may also include one or more coil loops of a charging coil disposed at a tool component according to one of the examples shown in FIG. 8A to 8C and another one or more coil loops of the same charging coil disposed at the tool component according to another one of the examples shown in FIG. 8A to 8C. The tool component 806 may be any component of a tool, such as for example, a battery or handle.

Figure 9:
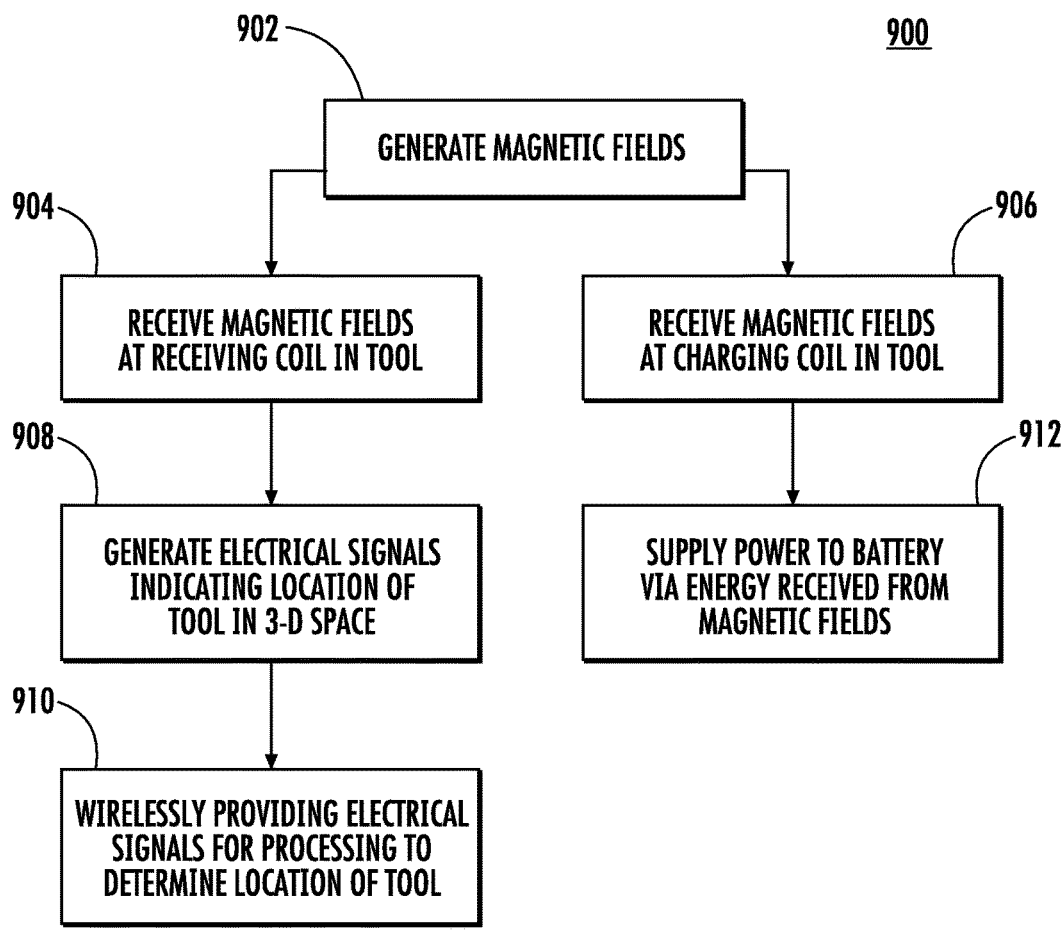
FIG. 9 is a flow diagram illustrating an example method of charging a wireless, battery-powered tool according to embodiments described herein.

FIG. 9 is a flow diagram illustrating an example method of charging a battery-powered medical tool used with an electromagnetic navigation system. As shown at block 902 of FIG. 9, the method 900 includes generating magnetic fields via wireless transmission signals. Each of the magnetic fields may be driven by a different frequency from an emitter coil of a wireless transmission device, such as for example a wireless transmission device positioned under a portion of patient anatomy to be operated upon.

As shown at block 904 of FIG. 9, the method 900 includes receiving magnetic fields at a receiving coil, disposed in the medical tool, which are used to receive the magnetic fields emitted by the one or more emitter coils and generate electrical signals indicative of a location of the medical tool in response to receiving the magnetic fields. Each magnetic field may be driven by a different frequency and generated from an emitter coil of a wireless transmission device. Magnetic fields may be generated via wireless transmission signals transmitted from separate wireless transmission devices.

As shown at block 906 of FIG. 9, magnetic fields are also received at a charging coil, electrically connected to a tool battery, which (i) receives energy from the magnetic fields and (ii) supplies the energy to the battery to charge the battery. The magnetic fields received at the charging coil are generated by the same wireless transmission devices which generate the magnetic fields used to locate the tool in 3-D space. The magnetic fields may be received at a charging coil when the magnetic field passes through a surface of the charging coil. The magnetic fields may be received by a single charging coil disposed at the battery, the handle portion or another portion of the tool. Alternatively, magnetic fields may be received by multiple charging coils disposed at the same portion of the tool or at separate portions of the tool, such as for example, charging coils disposed at the battery and handle portion.

As shown at block 908 of FIG. 9, the method 900 includes generating, by the receiving coil, electrical signals indicative of a location of the tool in 3-D space. For example, in response to receiving the magnetic fields, the electrical signals may be generated by the receiving coil based on the amplitude and phase of the magnetic fields.

As shown at block 910 of FIG. 9, the electrical signals are provided by the medical tool to a signal processor for processing the electrical signals to determine the location of the medical tool in 3-D space. The electrical signals may be provided to the signal processor via a wireless interface disposed at the medical tool.

As shown at block 912 of FIG. 9, the method 900 includes supplying power to the battery via energy received from the magnetic fields. For example, when a number of magnetic field lines (i.e., magnetic flux) of a magnetic field pass through the surface of the charging coil, energy is transferred from the magnetic field to the charging coil via a current induced in the charging coil. Because the amount of energy the charging coil receives from the magnetic field is proportionate to the area of the surface of the charging coil, the energy the additional coil surface area enables an additional amount of energy sufficient to charge the tool for a lengthy procedure while maintaining maneuverability of the tool.

The methods provided can be implemented in a general purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer readable media). The results of such processing can be maskworks that are then used in a semiconductor manufacturing process to manufacture a processor which implements features of the disclosure.

The methods or flow charts provided herein can be implemented in a computer program, software, or firmware incorporated in a non-transitory computer-readable storage medium for execution by a general purpose computer or a processor. Examples of non-transitory computer-readable storage mediums include a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

It should be understood that many variations are possible based on the disclosure herein. Although features and elements are described above in particular combinations, each feature or element can be used alone without the other features and elements or in various combinations with or without other features and elements.

What is claimed is:

1. An electromagnetic navigation system comprising:
a first wireless transmission device having one or more emitter coils, each of the one or more emitter coils configured to generate a magnetic field; and
a wireless, battery-powered tool comprising:
   a receiving coil, disposed at the tool, configured to receive one or more magnetic fields emitted by the one or more emitter coils and generate electrical signals indicative of a location of the tool in response to receiving the one or more magnetic fields;
   a wireless interface configured to provide the electrical signals for processing to determine the location of the tool in three-dimensional (3-D) space;
   a battery configured to supply power to the tool; and
   one or more charging coils electrically connected to the battery, each of the one or more charging coils configured to (i) receive energy from the one or more magnetic fields and (ii) supply the energy to the battery to charge the battery,
   wherein the receiving coil is disposed at a first portion of the tool configured to be inserted into patient anatomy during operation of the tool, and
   the battery and the one or more charging coils are disposed at a second portion of the tool configured to remain external to the patient anatomy during operation of the tool.

2. The system of claim 1, wherein the one or more charging coils is wound in a plurality of loops.

3. The system of claim 2, wherein the one or more charging coils is disposed at the battery and is wound in the plurality of loops around a portion of the battery.

4. The system of claim 2, wherein the tool further comprises a handle and at least a portion of the one or more charging coils is wound in the plurality of loops on an exterior surface of the handle.

5. The system of claim 1, wherein the one or more charging coils includes a first charging coil disposed at the first portion of the tool and a second charging coil disposed at the second portion of the tool separate from the first portion of the tool.

6. The system of claim 5, wherein the first charging coil is disposed at the battery and the second charging coil is disposed at a handle of the tool.

7. The system of claim 1, wherein the first wireless transmission device is horseshoe-shaped and comprises a plurality of emitter coils each configured to transmit wireless signals and generate the one or more magnetic fields.

8. The system of claim 1, further comprising a second wireless transmission device, separate from the first wireless transmission device, configured to transmit wireless signals and generate one or more additional magnetic fields,
   wherein each of the one or more charging coils is further configured to (i) receive energy from the one or more additional magnetic fields, generated by the second wireless transmission device, passing through the one or more charging coils and (ii) supply the energy received from the one or more additional magnetic fields to the battery to charge the battery.

9. A wireless, battery-powered medical tool for use with an electromagnetic navigation system, the medical tool comprising:
   a receiving coil, disposed at the medical tool, configured to receive one or more magnetic fields emitted by one or more emitter coils and generate electrical signals indicative of a location of the medical tool in response to receiving the one or more magnetic fields;
   a wireless interface configured to wirelessly provide the electrical signals for processing to determine the location of the medical tool in three-dimensional (3-D) space;
   a battery configured to supply power to the medical tool; and
   one or more charging coils electrically connected to the battery, each of the one or more charging coils disposed at the medical tool and configured to: (i) receive energy from the one or more magnetic fields; and (ii) supply the energy to the battery to charge the battery,
   wherein the receiving coil is disposed at a first portion of the tool configured to be inserted into patient anatomy during operation of the tool, and
   the battery and the one or more charging coils are disposed at a second portion of the tool configured to remain external to the patient anatomy during operation of the tool.

10. The medical tool of claim 9, wherein the one or more charging coils is wound in a plurality of loops.

11. The medical tool of claim 10, wherein the one or more charging coils is disposed at the battery and is wound in the plurality of loops around a portion of the battery.

12. The medical tool of claim 10, further comprising a handle, wherein at least a portion of the one or more charging coils is wound in the plurality of loops on an exterior surface of the handle of the medical tool.

13. The medical tool of claim 9, wherein the one or more charging coils includes a first charging coil disposed at the first portion of the medical tool and a second charging coil disposed at the second portion of the medical tool separate from the first portion of the medical tool.

14. The medical tool of claim 13, wherein the first charging coil is disposed at the battery and the second charging coil is disposed at a handle of the medical tool.

15. A method of charging a wireless, battery-powered medical tool, the method comprising:
   receiving, at a receiving coil disposed at a first portion of the medical tool inserted into patient anatomy, one or more magnetic fields;
   receiving, at one or more charging coils disposed at a second portion of the medical tool external to the patient anatomy and electrically connected to a battery disposed at the second portion of the medical tool, the one or more magnetic fields;
   generating, by the receiving coil at the first portion of the medical tool inserted into the patient anatomy, electrical signals indicative of a location of the medical tool in three-dimensional (3-D) space in response to receiving the one or more magnetic fields;
   providing, via a wireless interface disposed at the medical tool, the electrical signals for processing to determine the location of the medical tool in 3-D space; and
   supplying, by the one or more charging coils at the second portion of the medical tool external to the patient anatomy, power to the battery via energy received from the one or more magnetic fields.

16. The method of claim 15, wherein the one or more charging coils is wound in a plurality of loops.

17. The method of claim 16, wherein the one or more charging coils is disposed at the battery and is wound in the plurality of loops around a portion of the battery.

18. The method of claim 16, wherein at least a portion of the one or more charging coils is wound in the plurality of loops on an exterior surface of a handle of the tool.

19. The method of claim 15, wherein the one or more charging coils includes a first charging coil disposed at the first portion of the tool and a second charging coil disposed at the second portion of the tool separate from the first portion of the tool.

20. The method of claim 19, wherein the first charging coil is disposed at the battery and the second charging coil is disposed at a handle of the tool.

* * * * *